United States Patent [19]

Bakel

[11] Patent Number: 4,475,942

[45] Date of Patent: Oct. 9, 1984

[54] N-PHOSPHONOMETHYLGLYCINE DERIVATIVES AND HERBICIDAL COMPOSITIONS CONTAINING THEM

[75] Inventor: Izhak Bakel, Ramat Gan, Israel

[73] Assignee: Geshuri Laboratories Ltd., Tel-Mond, Israel

[21] Appl. No.: 412,196

[22] Filed: Aug. 27, 1982

[30] Foreign Application Priority Data

Aug. 8, 1982 [IL] Israel ............................. 66494

[51] Int. Cl.³ ..................... A01N 57/18; C07F 9/30
[52] U.S. Cl. ................................. 71/86; 71/87; 71/88; 260/501.12; 548/116; 548/119; 548/190; 548/199; 548/348; 548/350; 548/351; 549/491

[58] Field of Search ............ 260/501.12; 548/190, 548/199, 348, 350, 351, 116, 119; 549/491; 71/86, 87

[56] References Cited

U.S. PATENT DOCUMENTS

| 3,160,632 | 12/1964 | Dock et al. | 544/337 |
|---|---|---|---|
| 3,799,758 | 3/1974 | Franz | 71/86 |
| 4,147,719 | 4/1979 | Franz | 260/501.12 |
| 4,315,765 | 0/1982 | Large | 71/87 |

*Primary Examiner*—Richard Raymond
*Attorney, Agent, or Firm*—Cushman, Darby & Cushman

[57] ABSTRACT

The invention provides diiminourea, isothiourea and diisothiourea salts of N-Phosphonomethylglycine. The invention also provides phytotoxic compositions containing the same.

20 Claims, No Drawings

N-PHOSPHONOMETHYLGLYCINE DERIVATIVES AND HERBICIDAL COMPOSITIONS CONTAINING THEM

The present invention relates to N-phosphonomethylglycine (hereinafter referred to as NPMG) derivatives, and herbicidal compositions containing them. More specifically, the present invention relates to a whole series of newly discovered mono- and bi-functional urea and thiourea NPMG salts which surprisingly exhibit phytotoxic properties equal to and even superior to the most effective NPMG derivative marketed to date.

The compound NPMG is known for more than twenty years and it can be prepared as mentioned in U.S. Pat. No. 3,160,632 (1961) by the oxidation of the corresponding aminophosphinic compound utilizing mercuric chloride and other oxidizing agents.

NPMG in itself is a very effective phytotoxicant or herbicide, however, because it is relatively insoluble in water and conventional organic solvents, it is not as readily amenable to commercial formulation as are its derivatives. It is therefore generally preferred to utilize the more readily soluble derivatives of this compound in which at least one of the hydrogens in the hydroxy groups of NPMG has been replaced to form a water soluble salt.

In Israel Pat. No. 37993 there are described and claimed compounds of the formula:

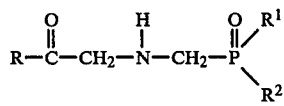

wherein R, $R^1$ and $R^2$ are independently selected from —OH and —$OR^6$, wherein $R^6$ is a salt-forming cation selected from the groups consisting of cations of alkali metals, alkaline earth metals, copper, zinc, manganese, nickel, ammonium and organic ammonium selected from primary-, secondary- and tertiary-alkyl, alkenyl and alkynyl-amines, none of these having more than two amine groups; primary aryl amines, primary aryl diamines and heterocyclic amines and the acid addition salts of strong acids of the above, wherein R, $R^1$ and $R^2$ are OH; provided that no more than two of R, $R^1$ and $R^2$ are —$OR^6$ when $R^6$ designates ammonium or organic ammonium (as above defined), and provided that when the organic group is an aryl group, the said ammonium salt is a primary amine salt, and mixtures of such salts, and provided that when said compound is other than an acid salt (said acid having a pK of 2.5 or less), no more than two of the groups R, $R^1$ and $R^2$ are —OH.

Included in the scope of said patent is N-phosphonomethylglycine mono isopropyl amine (NPMG.IPA) which is marketed by Monsanto Company under the trademark ROUNDUP® and which is recognized today as one of the leading herbicides in the world.

As is noted from said patent which is based on U.S. applications filed in 1971 and published in 1974, e.g. U.S. Pat. No. 3,799,758, it was believed and claimed by said patentee that only very specific salt forming cations, i.e. those "wherein $R^6$ is a salt-forming cation selected from the groups consisting of cations of alkali metals, alkaline earth metals, copper, zinc, manganese, nickel, ammonium and organic ammonium selected from primary-, secondary- and tertiary-alkyl, alkenyl and alkynyl-amines, none of these having more than two amine groups; primary aryl amines, primary aryl diamines and heterocyclic amines and the acid addition salts of the above" were suitable for forming commercial phytotoxicant compositions.

This is also consistant with the possible salt forming groups defined by said patentee in such related patents as U.S. Pat. Nos. 3,455,675 and 3,556,762 dating back to applications filed in the 1960's and the tens of patents filed by the same patentee in the late 1970's, including U.S. Pat. Nos. 3,835,000, 4,062,669, 4,084,953 and 4,147,719.

Thus despite the widefelt need for herbicidal compositions comparable to ROUNDUP® and the tens of patents relating to NPMG derivatives filed in the last years, since said 1974 patent no comparable NPMG derivative has been marketed by any company including Monsanto and this despite the fact that the annual worldwide sales of ROUNDUP® are reputed to be approaching the one billion dollar mark, which fact has spurred many companies to attempt without success to find a replacement for said compound.

According to the present invention there have been discovered a whole family of N-phosphonomethylglycine isothiourea, diisothiourea and diiminourea salts which salts are novel per se and which salts surprisingly are useful in phytotoxic compositions for controlling vegetation.

Thus, according to the present invention there are now provided N-Phosphonomethylglycine derivatives of the general formula I

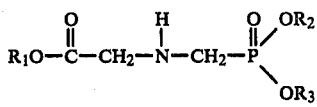

wherein
(a) $R_1$ and $R_2$ are hydrogen and $R_3$ is a salt forming cation of the general formula II

or $R_2$ is H and $R_1$ and $R_3$ are each a salt forming cation of the above formula II,
wherein $R_5$ is alkyl, allyl, vinyl, benzyl, furfuryl or a group of the formula

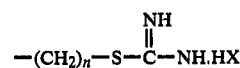

wherein n is 1–5 and X is halogen and $R_6$ and $R_7$ are independently H, alkyl, allyl or phenyl provided that only one of $R_6$ or $R_7$ may be alkyl, allyl, or phenyl, or $R_6$ and $R_7$ form together a group of the formula —$CH_2CH_2$—; or $R_7$ is hydrogen and $R_5$ and $R_6$ together form a group of the formula —CH=CH— or —$CH_2CH_2$—; or (b) $R_1$ and $R_2$ are H and $R_3$ is a salt forming cation of the general formula III

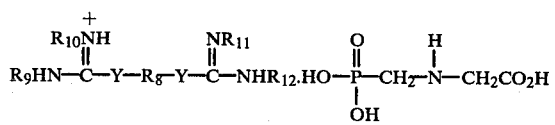

wherein Y is S or N, $R_8$ is a straight or branched chain alkylene radical having 1-12 carbon atoms and $R_9$, $R_{10}$, $R_{11}$ and $R_{12}$ are each independently H, alkyl, phenyl or allyl provided that only one of $R_9$ and $R_{10}$ may be alkyl, allyl or phenyl and only one of $R_{11}$ and $R_{12}$ may be alkyl, allyl or phenyl, or Y is S and $R_9$ and $R_{10}$ as well as $R_{11}$ and $R_{12}$ each together form a radical of the formula $-CH_2CH_2-$; or (c) $R_2$ is H and $R_1$ and $R_3$ together form a salt forming cation of the general formula IV

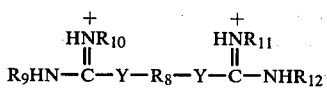

wherein $R_8$ and Y are as defined and $R_9$, $R_{10}$, $R_{11}$ and $R_{12}$ are each independently H, alkyl, phenyl or allyl provided that only one of $R_9$ and $R_{10}$ may be alkyl, allyl or phenyl and only one of $R_{11}$ and $R_{12}$ may be alkyl, allyl or phenyl.

The above novel mono- and bifunctional salts containing low molecular weight urea and isothiourea derivatives are water soluble, highly polar and exhibit comparable or even superior herbicidal activity when compared with the highly successful NPMG.IPA salts. It is believed that increasing the polarity and solubility of the NPMG salts improved herbicidal activity. Furthermore it has been found that the said bifunctional salts of the present invention exhibit superior drift properties, i.e. have a lesser tendency to drift after application than does the ROUNDUP ®. This tendency may be attributed in part to the higher molecular weight of said bifunctional derivatives. Thus the present invention provides a whole new class of highly effective and needed herbicidal compositions which are neither taught nor suggested by the prior art despite the widefelt need for such compounds and compositions and the extensive research carried out with regard to NPMG and its derivatives.

The monofunctional isothiourea salts of the above formula are those prepared from low molecular weight isothiourea, i.e. having a molecular weight below 600 such as: S-Methyl Isothiourea, S-Ethyl Isothiourea, S-Vinylisothiourea, S-Allylisothiourea, S-propylisothiourea, S-n-Butyl isothiourea, S-isobutylisothiourea, S-Pentylisothiourea, S-Benzylisothiourea, S-p-Chlorobenzylisothiourea, 2-aminothiazole, 2-amino-2-thiazoline, S-methylethyleneisothiourea, S-ethylethyleneisothiourea, S-allylethyleneisothiourea, S-methyl-N-allylisothiourea, S-Benzyl-ethylene-isothiourea, S-Benzyl-N-Allylisothiourea, S-methyl-N-methylisothiourea, S-allyl-N-Methylisothiourea, S-benzyl-N-methylisothiourea, S-Methyl-N-Phenylisothiourea, S-benzyl-N-phenylisothiourea, S-allyl-N-phenylisothiourea, S-ethyl-N-ethylisothiourea and the like.

The bifunctional Diisothiourea and Diiminourea salts of the above formula are those prepared from low molecular weight Diisothiourea and Diiminourea i.e. having a molecular weight below 600 such as: Ethane-1,2-diisothiourea, propane-1,2-diisothiourea, propane-1,3-diisothiourea, butane-1,4-diisothiourea, Pentane-1,5-diisothiourea, Ethane-1,2 di-(N,N'-dimethyl)isothiourea, Butane-1,4 di-(N,N'-diethyl)isothiourea, Ethane-1,2 di-(N,N'diallyl)isothiourea, Propane-1,3 di-(N,N'diallyl)isothiourea, Ethane-1,2 di-ethyleneisothiourea, Propane-1,3-di-ethyleneisothiourea, Ethane-1,2 di-(N,N'-diphenyl)isothiourea, Propane-1,3-di(N,N'-diphenyl)isothiourea, 2-Butene-1,4 diisothiourea, N,N'-ethylene diguanidine, N,N'-propylene diguanidine and N,N'-Butylene diguanidine.

Preferred NPMG isothiourea salts are those of the above formula I wherein $R_1$ and $R_2$ are hydrogen and $R_3$ is a salt forming cation of the general formula II, in which $R_6$ and $R_7$ are hydrogen and $R_5$ is selected from the group consisting of methyl, ethyl, propyl, butyl, allyl or benzyl; those of the above formula I wherein $R_1$ and $R_2$ are hydrogen and $R_3$ is a salt forming cation of the general formula II in which $R_6$ and $R_7$ form together a group of the formula $-CH_2CH_2-$ and $R_5$ is as defined; and those of the above formula I wherein $R_1$ and $R_2$ are hydrogen and $R_3$ is a salt forming cation of the general formula II in which $R_7$ is hydrogen and $R_5$ and $R_6$ together form a group of the formula $-CH=CH-$.

Especially preferred compounds are those wherein the isothiourea is S-methylisothiourea, i.e., wherein $R_5$ is $CH_3$ and $R_6$ and $R_7$ are H; the isothiourea is S-allylisothiourea i.e. wherein $R_5$ is $-CH_2-CH=CH_2$ and $R_6$ and $R_7$ are H; and the isothiourea is 2-aminothiazole i.e., wherein $R_7$ is H and $R_5$ and $R_6$ form together a group of the formula $-CH=CH_2-$.

Preferred NPMG diisothiourea and diiminourea salts are those of the above formula I wherein $R_1$ and $R_2$ are H and $R_3$ is a salt forming cation of the general formula III

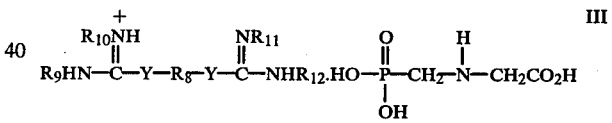

in which Y is S or N, $R_8$ is a straight or branched chain alkylene radical having 1-12 carbon atoms and $R_9$, $R_{10}$, $R_{11}$ and $R_{12}$ are each independently H, alkyl, phenyl or allyl provided that only one of $R_9$ and $R_{10}$ may be alkyl, allyl or phenyl and only one of $R_{11}$ and $R_{12}$ may be alkyl, allyl or phenyl.

Also preferred are those salts of the above formula I wherein $R_2$ is H and $R_1$ and $R_3$ together form a salt forming cation of general formula IV

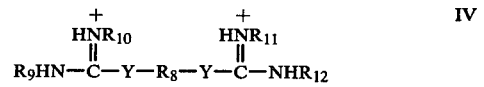

in which Y is S or N, $R_8$ is selected from the group consisting of ethylene, 1,2-propylene, 1,3-propylene and 1,4-butylene and $R_9$, $R_{10}$, $R_{11}$ and $R_{12}$ are each hydrogen.

Especially preferred compounds are those wherein the diisothiourea is Ethane-1,2-diisothiourea, i.e. wherein $Y=S$, $R_9$, $R_{10}$, $R_{11}$ and $R_{12}$ are H and $R_8$ is ethylene; the diisothiourea is propylene-1,3-diisothiourea i.e. wherein $Y=S$, $R_9$, $R_{10}$, $R_{11}$ and $R_{12}$ are all H and $R_8$ is propylene; the diiminourea is N,N'- ethylenediguanidine i.e. wherein Y=N, $R_9$, $R_{10}$, $R_{11}$ and $R_{12}$ are H and $R_8$ is ethylene and the diiminourea is N,N'-propylene diguanidine i.e. wherein Y=N, $R_9$, $R_{10}$, $R_{11}$ and $R_{12}$ are H and $R_8$ is propylene.

The compounds of this invention are readily prepared from NPMG by reacting the latter in water with sodium hydroxide to form the sodium salt, and treating the sodium salt with substituted isothiourea hydrohalide or diisothiourea DiHydrohalide or Diiminourea Dihydrohalide and heating the mixture until a clear solution is obtained. Alternatively the NPMG can be reacted directly with the above urea derivatives in the presence of propylene oxide and proceeding as described above. In case the free urea derivatives are available (such as ethylene diguanidine, 2-aminothiazole and the like) the NPMG salts are prepared by forming an admixture of said acid and the appropriate free urea derivatives in water and heating until a clear solution is obtained.

The Diiminourea NPMG salts can be obtained also by oxidation of Di-[N-(Phosphonomethyl)Iminodiacetic]Diiminourea salts with an oxidizing agent such as hydrogen peroxide or a free oxygen containing gas with catalyst such as activated carbon or metal catalyst.

In Israel Pat. No. 42393 there is described and claimed a process for the production of N-phosphonomethylglycine which comprises forming an admixture of N-(phosphonomethyl)inimodiacetic acid, water and an oxidizing agent and heating said admixture to a temperature at which said oxidizing agent and said N-(phosphonomethyl)iminodiacetic acid react to produce said N-phosphonomethylglycine.

Similarly in Israel Pat. No. 47202 there is described and claimed a process for the production of N-phosphonomethyl glycine which comprises contacting an aqueous solution of N-phosphonomethylimino diacetic acid with a molecular oxygen-containing gas at a temperature sufficiently elevated to initiate and sustain reaction and in the presence of a catalyst consisting essentially of activated carbon.

The novel Diiminourea NPMG compounds of the present invention can be prepared in a manner similar to that described in said patents.

Isothiourea and diisothiourea salts are in general readily formed by heating or refluxing thiourea or a substituted thiourea and the desired alkyl halide either without solvent or in alcoholic solvent. The biiminourea derivatives can be prepared from the appropriate diamine by reaction with O-methylisourea sulphate or cyanamide under suitable reaction conditions. All of the above methods are known per se in the art and need not be further described herein.

The compounds of the present invention can be used individually as an admixture of two or more compounds or in admixture with an adjuvant, and are effective as post emergent phytotoxicants or herbicides characterized by broad spectrum activity, i.e. they control the growth of a wide variety of plants including but not limited to ferns, conifer (pine, fir and the like) aquatic, monocotyledone and dicotyledons.

While the invention will now be described in connection with certain preferred embodiments in the following examples it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In the following examples throughout the specification, parts and percents are by weight unless otherwise indicated.

EXAMPLE 1

General procedures for preparing isothiourea, diisothiourea and diiminourea salts of NPMG.

(a) A reaction vessel was charged with 20 ml of water, 0.02 mole NPMG and 0.02 mole NaOH. The vessel was agitated until dissolution was completed. Then 0.02 mole of hydrohalide urea derivatives was added and a clear solution resulted. The solution was concentrated on a steam bath at reduced pressure, and the residue was heated with ethanol. Filtration and drying produced a white solid.

(b) A reaction vessel was charged with 20 ml of water, 0.02 mole NPMG and 0.02 mole hydrohalide urea derivatives. The vessel was heated gently in a water bath and 10 ml of propylene oxide was added. The mixture was stirred for one hour then washed with ether and the resulting phases were separated. The aqueous phase was then stripped and the residue was heated with ethanol. Filtration and drying produced white solid.

(c) A mixture of 0.02 mole NPMG, 25 parts of water and 0.02 mole free urea derivatives was agitated in a suitable reaction vessel at 40° C. After dissolution was completed the solution was concentrated on a steam bath at reduced pressure. The residue was washed with ethanol and dried yielding a white solid.

Following either procedure A or B the following salts were prepared:

S-Methylisothiuronium NPMG—white solid m.p. −194° C. (dec.) NMR (D$_2$O, δ, ppm, relative to HOD): −2.2 (s, 3H, CH$_3$): −1.55 (d, 2H, J=13 Hz) −1.05 (S, 2H)

S-Ethylisothiouronium NPMG—white solid m.p. −185° C. (dec.) NMR (D$_2$O, δ, ppm, relative to HOD): −3.5 (t, 3H, CH$_3$); −1.77 (q, 2H); −1.63 d, 2H, J=13 Hz); −1.1 (S, 2H)

Ethane-1,2 Diisothiuronium Di-NPMG—white solid m.p −177° (dec.) NMR (D$_2$O, δ, ppm, relative to HOD): −1.63 (d, 4H, J=13 Hz): −1.4 (S, 4H, —SCH$_2$CH$_2$S—); −1.12 (S, 4H).

Ethane-1,2-Diethylene diisothiuronium Di-NPMG. white solid m.p. 188° C. (dec). NMR (D$_2$O, δ, ppm, relative to HOD): −1.66 (d, 4H, J=13 Hz); −1.36 (S, 4H, —SCH$_2$CH$_2$S—); 1.1 (S. 4H); −0.9 (S, 8H, —N—CH$_2$CH$_2$N).

Ethane-1,2 Diisothiuronium NPMG: white solid m.p. −135° C. (dec.) NMR (D$_2$O, δ, ppm, relative to HOD): −1.77 (d, 2H, J=13 Hz); −1.45 (S, 2H) −1.27 (S, 2H): −1.07 (S, 2h).

N'N-ethylene diguanidinium Di NPMG: white solid NMR (D$_2$O, δ, ppm, relative to HOD): −1.72 (d, 4H, J=13 Hz): −1.24 (S, 4H, —NCH$_2$CH$_2$N—); −1.12 (s. 4H).

S-Allyl isothiuronium NPMG—white solid m.p −174° C. (dec.)

S-Benzyl isothiuronium NPMG—white solid m.p. 191° C. (dec.)

S-Butyl isothiuronium NPMG—white solid

S-Methyl-N-Phenyl isothiuronium NPMG—white solid m.p. 185° C. (dec.)

S-Benzyl-ethylene isothiuronium NPMG—white solid

S-allyl-N-Phenyl isothiuronium NPMG—white solid m.p. 198° C. (dec.)

S-Methyl-N-Methyl isothiuronium NPMG—white solid

S-ethyl-N-phenyl isothiuronium NPMG—white solid

S-Methyl-ethylene isothiuronium NPMG—white solid

Ethane-1,2-diisothiuronium hydrobromide NPMG—white solid m.p. 147° (dec.)

Following Procedure C 2-aminothiazolium NPMG was prepared: white solid NMR (D$_2$O, δ, ppm, relative to HOD): +2,3 (d, 1H, J=5 Hz); +1.93 (d, 1H, J=5 Hz); −1.07 (S, 2H); −1.6 (d, 2H, J=13 Hz).

EXAMPLE 2

The post-emergence herbicidal activity of various compounds of this invention is demonstrated as follows:

| PLANT RESPONSE | INDEX | PLANT RESPONSE | INDEX |
|---|---|---|---|
| No injury | 0 | Severe injury | 3 |
| Slight injury | 1 | Killed | 4 |
| Moderate injury | 2 | | |

The plant species utilized in these tests are identified by letter in accordance with the following legend:
A. PASPELON PASPOLOIDES
B. CHLORIS GAYAMA
C. PHALARIS PARADOXA
D. RUBUS CONESENES
E. ERAGROSTIS BIPINNATA
F. IMPEROTA CYLINDRICA
G. ANDROPOGONE HIRTUM
H. CYPERUS ROTUNDUS
I. INULA VISCOSA
J. PHROGMITES COMMUNIS
K. LYGEUM SPARTUM
L. PANICUM REPENS
M. CYNODON DACTYLON
N. SORGHUM HALEPENSE
O. CONVOLVULUS ARVENSIS
P. POLYGONNUM EQVISELIFORME

TABLE 1

| Compound | A | B | C | D | E | F | G | H | I | J | K | L | M | N | O | P |
|---|---|---|---|---|---|---|---|---|---|---|---|---|---|---|---|---|
| I | 2 | 2 | 2 | 2 | 1 | 2 | 2 | 3 | 2 | 1 | 1 | 2 | 2 | 2 | 2 | 2 |
| II | 2 | 2 | 2 | 2 | 1 | 2 | 2 | 3 | 2 | 1 | 2 | 2 | 2 | 2 | 2 | 2 |
| III | 2 | 3 | 2 | 1 | 1 | 2 | 2 | 3 | 3 | 1 | 1 | 2 | 2 | 2 | 3 | 3 |
| IV | 3 | 3 | 2 | 2 | 2 | 3 | 3 | 3 | 3 | 1 | 2 | 2 | 2 | 2 | 3 | 3 |
| V | 2 | 2 | 1 | 1 | 1 | 2 | 2 | 2 | 3 | 1 | 1 | 2 | 1 | 2 | 2 | 2 |
| VI | 3 | 3 | 2 | 1 | 2 | 3 | 3 | 3 | 3 | 1 | 1 | 2 | 3 | 3 | 3 | 3 |
| VII | 3 | 3 | 2 | 2 | 1 | 3 | 3 | 3 | 3 | 1 | 2 | 2 | 1 | 2 | 3 | 3 |
| VIII | 2 | 2 | 2 | 1 | 1 | 2 | 2 | 3 | 3 | 2 | 1 | 2 | 1 | 2 | 3 | 2 |
| IX | 2 | 2 | 2 | 1 | 1 | 3 | 3 | 3 | 3 | 1 | 1 | 2 | 2 | 2 | 3 | 3 |

The active ingredients are applied in spray to 21 day old specimens of various plant species. The spray, a water or organic solvent-water solution containing active ingredient and a surfactant (75 parts cationic detergent and 2.5 parts of nonionic one), is applied to the plants in different sets of pans at several rates (kilogram per dunam) of active ingredient. The treated plants are placed in a greenhouse and the effects are observed and recorded after approximately 2 weeks as is indicated in Table 1.

The post-emergence herbicidal activity index used in Table 1 is as follows:

The following are the compounds referred to by the Roman numerals in the table:

| ROMAN NUMERAL | COMPOUND NAME | ACTIVE INGREDIENT MOLE/L. |
|---|---|---|
| I | S-METHYL ISOTHIURONIUM NPMG | 0.043 |
| II | S-ETHYL ISOTHIURONIUM NPMG | 0.043 |
| III | S-ALLYL ISOTHIURONIUM NPMG | 0.043 |
| IV | ETHANE-1,2 DIISOTHIURONIUM DI-NPMG | 0.0215 |
| V | ETHANE-1,2 DIETHYLENE DIISOTHIURONIUM DI-NPMG | 0.0215 |
| VI | ETHANE-1,2 DIISOTHIURONIUM NPMG | 0.043 |
| VII | N,N'—ETHYLENE DIGUANIDINE - DI-NPMG | 0.0215 |
| VIII | 2-AMINO THIAZOLIUM NPMG | 0.043 |
| IX | MONO ISOPROPYL AMINE (ROUNDUP). | 0.043 |

It is to be noted that the above tabulated results were achieved when comparing two moles of active salt of compounds I, II, III, VI, VIII and IX with one mole of active salt of compounds IV, V and VII and thus it is clear that a herbicidal composition containing one mole of compounds IV, V and VII is superior to a composition containing one mole of the prior art mono-isopropyl amino compound.

The compositions of this invention provide a wide spectrum of weed control and are also extremely useful as general herbicides as well as in controlling unwanted plants in orchards, tree farms and various crops. For example, it has been found that by directing a spray of the compositions of this invention at the unwanted plants while essentially presenting such spray from contacting the leaves of trees, that such unwanted plants are controlled while there is no apparent injury to the trees. In such directed spraying, the spray can fall on the woody portion of the fruit tree or other tree without any apparent effect. Thus, the directed spray method of control is useful with crops such as plantation crops, i.e., rubber, coffee, bananas, tea, etc. and in orchards such as citrus fruits, apples, peaches, pears, nuts, olive, in vineyards and in bramble crops and in nursery crops to control the undesired plants; and in crops such as cotton, soybeans, sugarcane and the like.

The compositions of this invention are also useful for control of weeds between cropping seasons, for the renovation of stale seed beds and the like.

In applying the compositions of this invention to the plants which it is desired to control, it has been found to be desirable that the plant be emerged from the ground and even more desirable, that the plant be at least at the 2 leaf stage for maximum effect.

It has been found that when the plants to be controlled have a portion of their growth above the ground or water, and the above-ground or above-water portion of the plant contacted with the herbicidal compositions of this invention at appropriate rates, the herbicide is translocated to kill such plant parts which are below the ground or water surface.

One can obtain limited selectivity in crops such as cotton, soybeans, sugar cane and like crops by directing the spraying of a composition of this invention at a selected concentration on vegetation around the base of such plants with minimal spray contact with the leafy portions of such crop plants. The directed spraying can be done with or without a protective device to prevent contact of the spray with the leaves of such crop plants.

A non-exhaustive list of some of the plant species which are controlled by the compositions of this invention, in addition to those shown in Table 1, are set forth below:

ter, a wetting agent, a dispersing agent, an emulsifying agent or any suitable combination of these. From the viewpoint of economy and convenience, water is the preferred diluent, particularly with the highly water-soluble N-phosphonomethylglycine isothiourea diisothiourea and diiminourea salts of the present invention. With these derivatives, solutions containing as high as 60% by weight of active materials can be readily prepared.

The phytotoxicant compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene sulfated fatty alcohols, amines or acid amides, sulfated or sulfonated fatty acid esters petroleum sulfonates, sulfonated vegetable oils, polyoxyethylene derivatives of alkylphonols (particularly isooctylphenol and nonylphenol), Mono-fatty di-alkyl amine oxide, and mono-fatty di-alkyl benzalkonium chloride.

Preferred dispersants are methyl cellulose, polyvinyl alcohol, sodium lignin sulfonates, polymeric alkyl naphthalene sulfonates and sodium naphthalene sulfonate.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Ex-

| | |
|---|---|
| CRAMBE HISPANICA | EUPHORIA CYBIRENSIS |
| ERUCARIA MYAGROIDES | CROZOPHORA TINCTORIA |
| HIRCHFELDIA INCANA | ERODIUM MOSCHATUM |
| DIPLOTAXIS ERUCOIDES | RANUNCULUS TRACHYCARFUS |
| AMARANTHUS RETROFLEXUS L | RANUNCULUS ARVENSIS |
| AMARANTHUS LIVIDUS L | SOLANUM ELEAGNIFOLIUM |
| AMARANTHUS ALBUS L | POLYGONUM EQUISELIFORME |
| AMARANTHUS GRAECIZANS | ANTHEMIS PSEUDOCOTULA |
| ECHINOCHLOA COLONUM | ANTHEMIS MELANOLEPIS |
| CYNODON DACTYLON | CARTHAMUS TENUIS |
| PHALARIS | ORMENIS MIXTA |
| LOLIUM RIGIDUM | EROGERON CRISPUS |
| CHENOPODIUM MURALE | SCORPIURUS MURICATA |
| BETA VULGARIS | HYMENOCARPUS CIRCINNATUS |
| CHENOPODIUM OPULIFOLIUM | SECURIGERA SECURIDACA |
| SONCHUS OLERACEUS | DIGITARIA SANGUINALIS |
| XANTHIUM STRUMARIUM | SORGHUM HALEPENSE |
| CALENDULA ARVENSIS | SETARIA VERTICILLATA |
| RIDULFIA SEGETUM | AVENA STERILIS |
| TORDYLIUM AEGYPTIACUM | AMMI MAJOR |
| BUPLEVRUM PERFOLIATUM | CONVOLVULVUS ARVENSIS |
| TRIGONELLA | |
| VICIA VULGARE | |

The phytotoxicant compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents known per se to provide compositions in the form of finely-divided particulate solids, pellets, solutions, dispersions or emulsions. Thus the active ingredient can be used with an adjuvant such as a finely-divided solid, a liquid or organic origin, waamples of such extenders include kaolinites, and synthetic magnesium silicate. The water-dispersible compositions of this invention usually contain from about 10 to about 90 parts by weight of active ingredient, from about 0.5 to 20 parts by weight of wetting agent, from about 0.5 to 20 parts by weight of dispersant and from 5.0 to about 90 parts by weight of inert, solid extender, all parts being by weight of the total composition.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 10 to 95 parts active ingredient, about 2 to 50 parts surface active agent and about 4 to 90 parts solvent, all parts being by weight based on the total weight of emulsifiable oil.

Although compositions of this invention can also contain other additives, for example fertilizers, phytotoxicants and plant growth regulants, pesticides and the like used as adjuvants or in combination with any of the above-described adjuvants, it is preferred to employ the compositions of this invention, alone with sequential treatments with the other phytotoxicants, fertiliziers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals used in combination with the active ingredients of this invention either simultaneously or sequentially include for example triazines, ureas, carbamates, acetamides, acentanilides, uracils, acetic acids, phenols thiolcarbamates, triazoles, benzoic acids, nitriles and the like such as:
3-amino-2,5-dichlorobenzoic acid
3-amino-1,2,4-triazole
2-methoxy-4-ethylamino-6-isopropylamino-s-triazine
2-chloro-4-ethylamino-6-isopropylamino-2-triazine
2-chloro-N,N-diallylacetamide
2-chloroallyl diethyldithiocarbamate
N'-(4-chlorophenoxy)phenyl-N,N-dimethylurea
1,1'-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4-4'bipyridinium salt
2-chloro-4-6 bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanecarsonate
N-(1,1-dimethylpropynyl)-3,5-dichlorobenzamide Fertilizers useful in combination with the active ingredients include for example ammonium nitrate, urea, potash and superphosphate.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.1 to about 50 or more kilogram per dunam. In applications for the control of aquatic plants, the active ingredients are applied in amounts of from about 0.1 parts per million to about 2000 parts per million, based on the aquatic medium. An effective amount for phytotoxicant or herbicidal control is that amount necessary for overall or selective control, i.e., a phytotoxic or herbicidal amount. It is believed that one skilled in the art can readily determine from the teachings of this specification, including examples, the approximate application rate.

The compositions of this invention are also useful as harvesting aids in many crops. Thus, for example, the crop could be sprayed with the compositions of this invention to reduce the bulk of unwanted material and make the harvesting of the crops easier. Such crops are, for example, peanuts, soybeans, and root crops such as potatoes, sugar beets, red beets and the like.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come with the meaning and range of equivalency of the claims are therefore intended to be embraced therein.

What is claimed is:
1. N-Phosphonomethylglycine derivatives of the general formula I

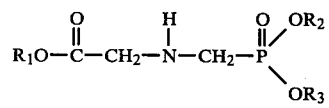

wherein
(a) $R_1$ and $R_2$ are hydrogen and $R_3$ is a salt forming cation of the general formula II $$\overset{+}{R_6NH} \\ R_7HN-\overset{\|}{C}-S-R_5 \quad \text{II}$$

or $R_2$ is H and $R_1$ and $R_3$ are each a salt forming cation of the above formula II, wherein $R_5$ is alkyl, allyl, vinyl, benzyl, furfuryl or a group of the formula $$-(CH_2)_n-S-\overset{NH}{\overset{\|}{C}}-NH.HX$$

wherein n is 1–5 and X is halogen and $R_6$ and $R_7$ are independently H, alkyl, allyl or phenyl provided that only one of $R_6$ or $R_7$ may be alkyl, allyl, or phenyl, or $R_6$ and $R_7$ form together a group of the formula $-CH_2CH_2-$; or $R_7$ is hydrogen and $R_5$ and $R_6$ together form a group of the formula $-CH=CH-$ or $-CH_2CH_2-$; or (b) $R_1$ and $R_2$ are H and $R_3$ is a salt forming cation of the general formula III $$\overset{+}{R_{10}NH} \quad \overset{NR_{11}}{} \quad O \quad H \\ R_9HN-\overset{\|}{C}-Y-R_8-Y-\overset{\|}{C}-NHR_{12}.HO-\overset{\|}{\underset{OH}{P}}-CH_2-\overset{|}{N}-CH_2CO_2H \quad \text{III}$$

wherein Y is S or N, $R_8$ is a straight or branched chain alkylene radical having 1–12 carbon atoms and $R_9$, $R_{10}$, $R_{11}$ and $R_{12}$ are each independently H, alkyl, phenyl or allyl provided that only one of $R_9$ and $R_{10}$ may be alkyl, allyl or phenyl and only one of $R_{11}$ and $R_{12}$ may be alkyl, allyl or phenyl, or Y is S and $R_9$ and $R_{10}$ as well as $R_{11}$ and $R_{12}$ each together form a radical of the formula $-CH_2CH_2-$; or (c) $R_2$ is H and $R_1$ and $R_3$ together form a salt forming cation of general formula IV $$\overset{+}{HN}-R_{14} \quad \overset{+}{HN}-R_{15} \\ R_{13}HN-\overset{\|}{C}-Y-R_8-Y-\overset{\|}{C}-NHR_{16} \quad \text{IV}$$

wherein $R_8$ and Y are as defined and $R_{13}$, $R_{14}$, $R_{15}$ and $R_{16}$ are each independently H, alkyl, phenyl or allyl provided that only one of $R_{13}$ and $R_{14}$ may be alkyl, allyl or phenyl and only one of $R_{15}$ and $R_{16}$ may be alkyl, allyl or phenyl.

2. N-Phosphonomethyl derivatives according to claim 1 wherein $R_1$ and $R_2$ are hydrogen and $R_3$ is a salt forming cation of the general formula II $$\overset{+}{R_6NH} \\ R_7HN-\overset{\|}{C}-S-R_5 \quad \text{II}$$

or $R_2$ is H and $R_1$ and $R_3$ are each a salt forming cation of the above formula II, wherein $R_5$ is alkyl, allyl, vinyl, benzyl, furfuryl or a group of the formula $$-(CH_2)_n-S-\overset{NH}{\overset{\|}{C}}-NH.HX$$

wherein n is 1–5, x is halogen and $R_6$ and $R_7$ are independently H, alkyl, allyl or phenyl provided that only one of $R_6$ or $R_7$ may be alkyl, allyl, or phenyl, or $R_6$ and $R_7$ form together a group of the formula $-CH_2CH_2-$, or $R_7$ is hydrogen and $R_5$ and $R_6$ together form a group of the formula $-CH=CH-$ or $-CH_2CH_2-$.

3. N-Phosphonomethylglycine derivatives according to claim 2, wherein $R_1$ and $R_2$ are hydrogen and $R_3$ is a salt forming cation of the general formula II, in which $R_6$ and $R_7$ are hydrogen and $R_5$ is selected from the group consisting of methyl, ethyl, propyl, butyl, allyl or benzyl.

4. N-Phosphonomethylglycine derivatives according to claim 2 wherein $R_1$ and $R_2$ are hydrogen and $R_3$ is a salt forming cation of the general formula II in which $R_6$ and $R_7$ form together a group of the formula $-CH_2CH_2-$ and $R_5$ is as defined.

5. N-Phosphonomethylglycine derivatives according to claim 2 wherein $R_1$ and $R_2$ are hydrogen and $R_3$ is a salt forming cation of the general formula II in which $R_7$ is hydrogen and $R_5$ and $R_6$ together form a group of the formula $-CH=CH-$.

6. N-Phosphonomethylglycine derivatives according to claim 3 wherein $R_6$ and $R_7$ are hydrogen and $R_5$ is methyl.

7. N-Phosphonomethylglycine derivatives according to claim 3 wherein $R_5$ is ethyl and $R_6$ and $R_7$ are hydrogen.

8. N-phosphonomethylglycine derivatives according to claim 3 wherein $R_5$ is allyl and $R_6$ and $R_7$ are hydrogen.

9. N-phosphonomethylglycine derivatives according to claim 1 wherein $R_1$ and $R_2$ are H, and $R_3$ is a salt forming cation of the general formula III $$\overset{+}{R_{10}-NH} \quad \overset{NR_{11}}{} \quad O \quad H \\ R_9HN-\overset{\|}{C}-Y-R_8-\overset{\|}{C}-NHR_{12}.HO-\overset{\|}{\underset{OH}{P}}-CH_5-\overset{|}{N}-CH_2CO_2H \quad \text{III}$$

in which Y is S or N, $R_8$ is a straight or branched chain alkylene radical having 1–12 carbon atoms and $R_9$, $R_{10}$, $R_{11}$ and $R_{12}$ are each independently H, alkyl, phenyl or allyl provided that only one of $R_9$ and $R_{10}$ may be alkyl, allyl or phenyl and only one of $R_{11}$ and $R_{12}$ may be alkyl, allyl or phenyl.

10. N-phosphonomethylglycine derivatives according to claim 1 wherein $R_1$ and $R_2$ are hydrogen and $R_3$ is a salt forming cation of the general formula III in which Y is S and $R_9$ and $R_{10}$ as well as $R_{11}$ and $R_{12}$ each together form a radical of the formula $-CH_2CH_2-$.

11. N-phosphonomethylglycine derivatives according to claim 1 wherein $R_2$ is H and $R_1$ and $R_3$ together form a salt forming cation of general formula IV $$\overset{+}{HN}-R_{14} \quad \overset{+}{HN}-R_{15} \\ R_{13}HN-\overset{\|}{C}-Y-R_8-Y-\overset{\|}{C}-NHR_{16} \quad \text{IV}$$

in which Y is S or N, $R_8$ is a straight or branched chain alkylene radical having 1–12 carbon atoms and $R_{13}$, $R_{14}$, $R_{15}$ and $R_{16}$ are each independently H, alkyl, phenyl or allyl provided that only one of $R_{13}$ and $R_{14}$ may be alkyl, allyl or phenyl and only one of $R_{15}$ and $R_{16}$ may be alkyl, allyl or phenyl.

12. N-phosphonomethylglycine derivatives according to claim 9 wherein $R_8$ is selected from the group consisting of ethylene, 1,2-propylene, 1,3-propylene and 1,4-butylene and $R_9$, $R_{10}$, $R_{11}$ and $R_{12}$ are each hydrogen.

13. N-phosphonomethylglycine derivatives according to claim 11 wherein $R_8$ is selected from the group consisting of ethylene, 1,2-propylene, 1,3-propylene and 1,4-butylene and $R_{13}$, $R_{14}$, $R_{15}$ and $R_{16}$ are each hydrogen.

14. N-phosphonomethylglycine derivatives according to claim 9 wherein Y is S, $R_8$ is ethylene and $R_9$, $R_{10}$, $R_{11}$ and $R_{12}$ are each hydrogen.

15. N-phosphonomethylglycine derivatives according to claim 9 wherein Y is S, $R_8$ is propylene and $R_9$, $R_{10}$, $R_{11}$ and $R_{12}$ are each hydrogen.

16. N-phosphonomethylglycine derivatives according to claim 9 wherein Y is N, $R_8$ is ethylene and $R_9$, $R_{10}$, $R_{11}$ and $R_{12}$ are each hydrogen.

17. N-phosphonomethylglycine derivatives according to claim 9 wherein Y is N, $R_8$ is propylene and $R_9$, $R_{10}$, $R_{11}$ and $R_{12}$ are each hydrogen.

18. A phytotoxic composition comprising an adjuvant and an effective amount of one or more N-phosphonomethylglycine derivatives as claimed in claim 1.

19. A method of controlling unwanted plants comprising applying to the plants in the post emergent state a herbicidal composition comprising a herbicidally effective amount of a compound according to claim 1.

20. A method according to claim 19 wherein the herbicidal composition is applied to the leaves of the plants.

* * * * *